US011276209B2

(12) United States Patent
Qi et al.

(10) Patent No.: US 11,276,209 B2
(45) Date of Patent: Mar. 15, 2022

(54) METHOD AND APPARATUS FOR SCATTER ESTIMATION IN POSITRON EMISSION TOMOGRAPHY

(71) Applicant: CANON MEDICAL SYSTEMS CORPORATION, Tochigi (JP)

(72) Inventors: Wenyuan Qi, Vernon Hills, IL (US); Yujie Lu, Vernon Hills, IL (US); Evren Asma, Vernon Hills, IL (US); Yi Qiang, Vernon Hills, IL (US); Jeffrey Kolthammer, Vernon Hills, IL (US); Zhou Yu, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 141 days.

(21) Appl. No.: 16/860,425

(22) Filed: Apr. 28, 2020

(65) Prior Publication Data
US 2021/0335023 A1    Oct. 28, 2021

(51) Int. Cl.
*G06T 11/00* (2006.01)
*A61B 6/03* (2006.01)
(Continued)

(52) U.S. Cl.
CPC ............ *G06T 11/008* (2013.01); *A61B 6/032* (2013.01); *A61B 6/037* (2013.01); *A61B 6/5205* (2013.01);
(Continued)

(58) Field of Classification Search
CPC ..... G06T 11/008; A61B 6/032; A61B 6/5205; A61B 6/037
See application file for complete search history.

(56) References Cited

U.S. PATENT DOCUMENTS

2004/0249260 A1* 12/2004 Wang .................. A61B 5/0077
600/407
2010/0310037 A1* 12/2010 Wang ...................... A61B 6/06
378/6
(Continued)

OTHER PUBLICATIONS

Klose, A. et al. "The inverse source problem based on the radiative transfer equation in optical molecular imaging", Journal of Computational Physics, vol. 202, Jan. 1, 2005, pp. 323-345.
(Continued)

*Primary Examiner* — Gandhi Thirugnanam
(74) *Attorney, Agent, or Firm* — Oblon, McClelland, Maier & Neustadt, L.L.P.

(57) ABSTRACT

The present disclosure relates to an apparatus for estimating scatter in positron emission tomography, comprising processing circuitry configured to acquire an emission map and an attenuation map, each representing an initial image reconstruction of a positron emission tomography scan, calculate, using a radiative transfer equation (RTE) method, a scatter source map of a subject of the positron emission tomography scan based on the emission map and the attenuation map, estimate, using the RTE method and based on the emission map, the attenuation map, and the scatter source map, scatter, and perform an iterative image reconstruction of the positron emission tomography scan based on the estimated scatter and raw data from the positron emission tomography scan of the subject.

20 Claims, 14 Drawing Sheets

(51) Int. Cl.
*A61B 6/00* (2006.01)
*G06T 7/00* (2017.01)

(52) U.S. Cl.
CPC .......... *A61B 6/5235* (2013.01); *G06T 7/0012* (2013.01); *G06T 2207/10081* (2013.01); *G06T 2207/10104* (2013.01); *G06T 2207/30004* (2013.01)

(56) References Cited

U.S. PATENT DOCUMENTS

| | | | |
|---|---|---|---|
| 2011/0060211 A1* | 3/2011 | Lorenzo | A61B 5/0071 600/411 |
| 2011/0184277 A1* | 7/2011 | Ripoll Lorenzo | G01N 21/6486 600/425 |
| 2015/0286785 A1* | 10/2015 | Hielscher | A61B 5/0073 382/131 |
| 2018/0014806 A1* | 1/2018 | Lu | A61B 6/5282 |
| 2018/0204356 A1* | 7/2018 | Xia | A61B 6/482 |
| 2018/0235562 A1* | 8/2018 | Petschke | A61B 6/032 |
| 2019/0066342 A1* | 2/2019 | Zhu | G06T 11/005 |
| 2019/0197740 A1* | 6/2019 | Lu | G06T 11/005 |
| 2020/0170601 A1* | 6/2020 | Gagnon | G06T 11/005 |
| 2020/0170607 A1* | 6/2020 | Yu | A61B 6/5282 |
| 2020/0340932 A1* | 10/2020 | Lu | G01N 23/046 |
| 2021/0282732 A1* | 9/2021 | Qi | A61B 6/5235 |
| 2021/0335023 A1* | 10/2021 | Qi | G06T 11/008 |

OTHER PUBLICATIONS

Jha, A. et al., "Joint reconstruction of activity and attenuation map using LM SPECT emission data", Proceedings of SPIE—The International Society for Optical Engineering, Mar. 2013, 10 pages.

Watson, C.C., et al., "A single scatter simulation technique for scatter correction in 3D PET," Three-Dimensional Image Reconstruction in Radiology and Nuclear Medicine, 1996, pp. 255-268.

Watson, C.C., "Extension of single scatter simulation to scatter correction of time-offlight PET," IEEE Transactions on Nuclear Science, vol. 54, No. 5, Oct. 2007, pp. 1679-1686.

Zaidi, H., "Scatter modelling and correction strategies in fully 3-D PET," Nuclear Medicine Communications, vol. 22, Jul. 15, 2001, pp. 1181-1184.

Lu. Y. et al., "A deterministic integral spherical harmonics method for scatter simulation in computed tomography," Physics of Medical Imaging, 2017, 8 pages.

\* cited by examiner

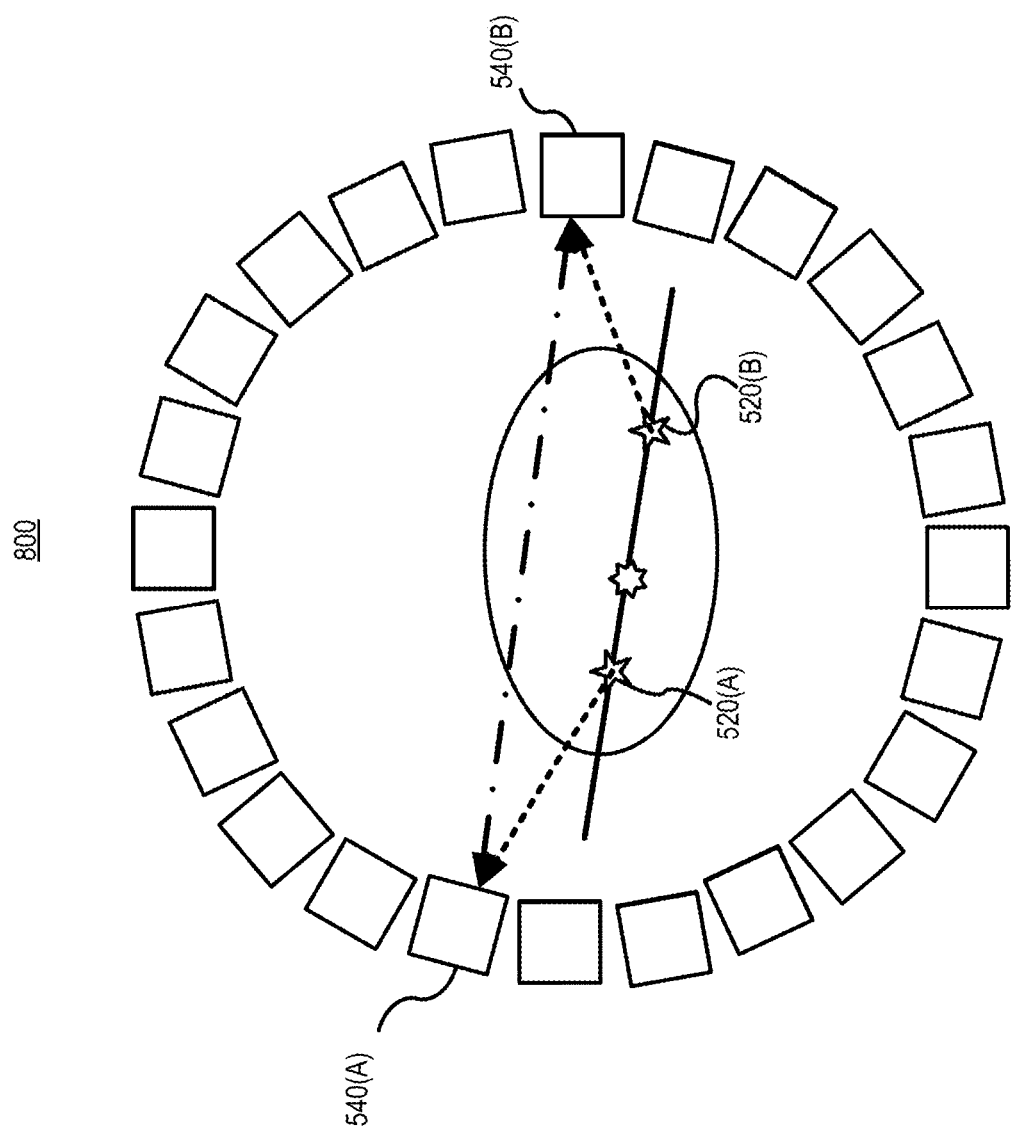

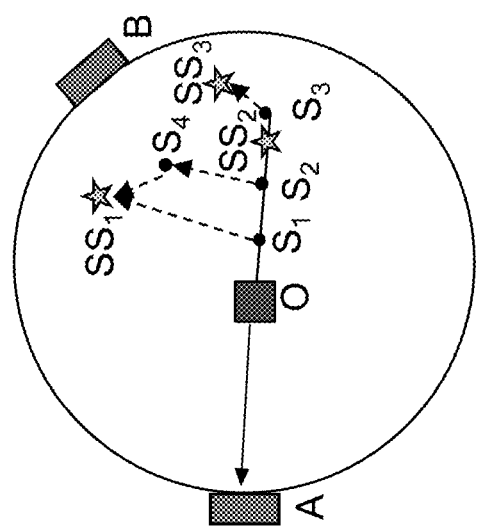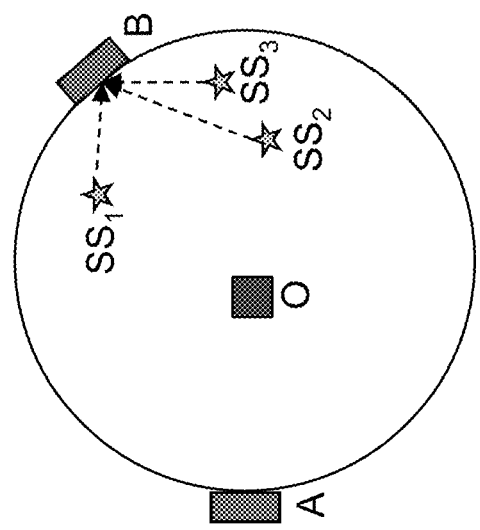
FIG. 6A
FIG. 6B ered by a computer, cause the computer to perform a method for reconstructing an image in positron emission tomography, comprising acquiring an emission map and an attenuation map, each representing an initial image reconstruction of a positron emission tomography scan, calculating, using a RTE method, a scatter source map of a subject

METHOD AND APPARATUS FOR SCATTER ESTIMATION IN POSITRON EMISSION TOMOGRAPHY

BACKGROUND FIELD OF THE DISCLOSURE

The present disclosure relates to scatter estimation and correction for positron emission tomography. This scatter estimation and correction can also find application in computed tomography, X-ray imaging, radiography, fluoroscopy, and angiography, for example.

DESCRIPTION OF THE RELATED ART

Positron emission tomography (PET) is an imaging method in nuclear medicine based on the use of a weak radioactively marked pharmaceutical (i.e., a tracer) to image certain features of a body. PET images display the spatial distribution of the radiopharmaceutical over time, thereby enabling a doctor or clinician to draw conclusions about metabolic activities or blood flow, for example.

In PET imaging, a tracer agent is introduced into the patient to be imaged (e.g., via injection, inhalation, or ingestion). After administration, the physical and bio-molecular properties of the agent cause it to concentrate at specific locations in the patient's body. The actual spatial distribution of the agent, the intensity of the region of accumulation of the agent, and the kinetics of the process from administration to its eventual elimination are all factors that may have clinical significance.

During this process, a tracer attached to the agent will emit positrons, which is the anti-matter equivalent of the electron. When an emitted positron collides with an electron, the electron and positron are annihilated, resulting in the emission of a pair of gamma rays each having an energy of 511 keV and the two gamma rays traveling at substantially 180 degrees apart.

The spatio-temporal distribution of the tracer is reconstructed via tomographic reconstruction principles by, for example, characterizing each detection event for its energy (i.e., amount of light generated), location, and timing. When two gamma rays are detected within a coincidence time window, they likely originate from the same positron annihilation event, and, therefore, are identified as being a coincidence pair. Drawing a line between their locations (i.e., the line-of-response (LOR)) one can determine the likely location of the positron annihilation event. The timing information can also be used to determine a statistical distribution along the LOR for the annihilation based on time-of-flight information of the two gamma rays. By accumulating a large number of LORs, tomographic reconstruction can be performed to determine a volumetric image of the spatial distribution of radioactivity (e.g., tracer density) within the patient.

Due to health concerns regarding exposure to radiation, clinicians in medical imaging strive to maintain radiation doses as low as reasonably achievable. This effort to maintain radiation doses as low as reasonably achievable motivates continued improvements in reconstructed image quality while decreasing the radiation doses and signal-to-noise ratios of the measured signals.

Scatter, for instance, is a main degrading factor in PET image reconstruction. Two main methods for scatter corrections —Monte Carlo simulation and Model-based single scatter simulation (SSS)—each have their respective shortcomings. The discrete nature of Monte Carlo simulation makes it inherently noisy, but this can be overcome by increasing the number of simulations. Performing a large number of Monte Carlo simulations, however, requires significant time and computational processing, making this approach often too slow for commercial implementation. As an alternative, SSS is relatively fast making it the preferred approach for commercial applications of PET scatter correction. SSS, however, is inherently inaccurate as it only includes single event scatter estimation and thus ignores higher order scatter.

Accordingly, improved methods are desired for performing PET scatter correction and thereby improving the image quality of PET images. Compared to current methods, these improved methods should have either improved accuracy or computational efficiency or both.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to scatter estimation in positron emission tomography using a radiative transfer equation.

According to an embodiment, the present disclosure further relates to an apparatus for reconstructing an image in positron emission tomography, comprising processing circuitry configured to acquire an emission map and an attenuation map, each representing an initial image reconstruction of a positron emission tomography scan, calculate, using a radiative transfer equation (RTE) method, a scatter source map of a subject of the positron emission tomography scan based on the emission map and the attenuation map, estimate, using the RTE method and based on the emission map, the attenuation map, and the scatter source map, scatter, and perform an iterative image reconstruction of the positron emission tomography scan based on the estimated scatter and raw data from the positron emission tomography scan of the subject.

According to an embodiment, the present disclosure further relates to a method for reconstructing an image in positron emission tomography, comprising acquiring, by processing circuitry, an emission map and an attenuation map, each representing an initial image reconstruction of a positron emission tomography scan, calculating, by the processing circuitry using a RTE method, a scatter source map of a subject of the positron emission tomography scan based on the emission map and the attenuation map, estimating, by the processing circuitry using the RTE method and based on the emission map, the attenuation map, and the scatter source map, scatter, and performing, by the processing circuitry, an iterative image reconstruction of the positron emission tomography scan based on the estimated scatter and raw data from the positron emission tomography scan of the subject.

According to an embodiment, the present disclosure further relates to a non-transitory computer-readable storage medium storing computer-readable instructions that, when executed by a computer, cause the computer to perform a method for reconstructing an image in positron emission tomography, comprising acquiring an emission map and an attenuation map, each representing an initial image reconstruction of a positron emission tomography scan, calculating, using a RTE method, a scatter source map of a subject of the positron emission tomography scan based on the emission map and the attenuation map, estimating, using the RTE method and based on the emission map, the attenuation map, and the scatter source map, scatter, and performing an iterative image reconstruction of the positron emission tomography scan based on the estimated scatter and raw data from the positron emission tomography scan of the subject.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3E is a schematic of gamma ray generation and detection of a two-sided first-order scatter event, according to an exemplary embodiment of the present disclosure;

FIG. 6A is an illustration of a calculated scatter source map, according to an exemplary embodiment of the present disclosure;

FIG. 6B is an illustration of estimated scatter flux at a detector B, according to an exemplary embodiment of the present disclosure;

DETAILED DESCRIPTION

Figure 1:
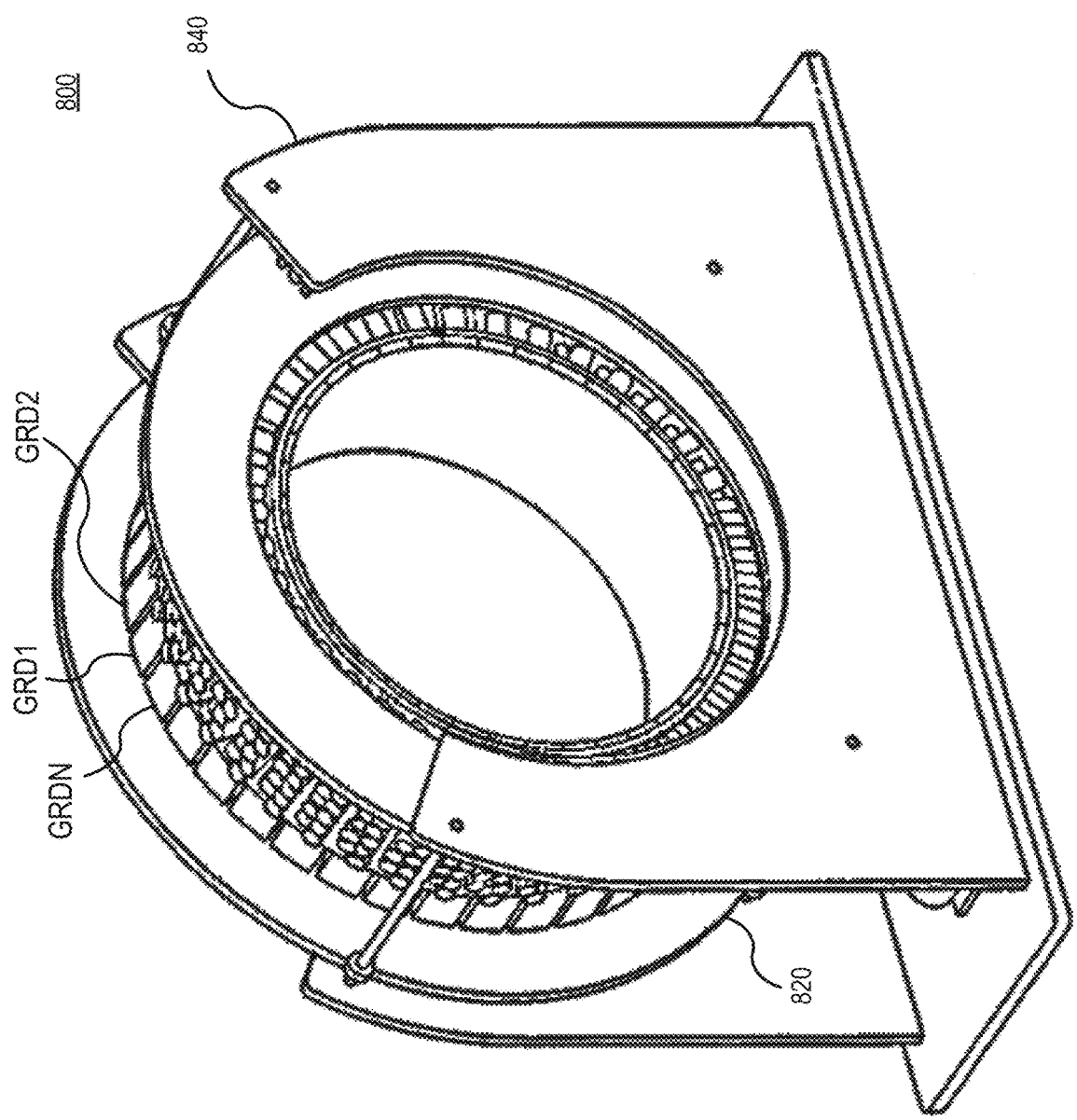
FIG. 1 is a perspective view of a positron emission tomography (PET) scanner, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

In positron emission tomography (PET), the measured coincidences include both true coincidences and a background signal (e.g., random coincidences). To improve the image quality of a reconstructed PET signal, it is desirable to estimate and account for this background signal. For example, the background signal can be accounted for by correcting the data using a baseline subtraction based on the estimated background signal, or, when a log-likelihood objective function is used to iteratively reconstruct a PET image, the log-likelihood expression can include a background-signal term based on the estimated background signal. The background signal includes counts due to random events and scatter events. In PET, the background signal is primarily made up of accidental coincidences, also known as randoms, and scatters.

For many annihilation events, only one photon of a pair of photons is detected because the other photon is absorbed or scattered out of plane of a PET detector ring. Further, some photons reaching the scintillating detectors of the PET detector ring are not detected due to a less than unity quantum efficiency of the detectors. Detection events in which only one of a pair of photons is detected can be referred to as "singles." If two singles from separate annihilations are detected within the coincidence timing window, then they are mistakenly registered as having arisen from the same annihilation. This is called an accidental coincidence (AC) event, also known as a random event. Stated differently, an AC event occurs when two unrelated singles are detected within a coincidence timing window.

Although most scattered photons in the body leave the detector plane undetected, some scattered photons are still detected and registered, resulting in an incorrect line-of-response (LOR). In certain implementations, some of these scattered events resulting in incorrect LORs can be removed by energy discrimination because photons lose a fraction of their energy during the Compton interaction giving rise to the scatter event. Even so, some scattered photons (scatters) and some random coincidences (randoms) will inevitably be recorded, and, thus, the background signal includes the randoms and the scatters.

Various corrections can be performed on the PET data, resulting in better image quality. For example, gamma rays are attenuated as they propagate through the patient, detector elements vary in their detection efficiency, and random and scattered coincidences are recorded along with the true coincidence events. Correcting for these effects improves the image quality, resulting in clinically useful images and accurate quantitative information from PET studies.

Gamma rays that encounter more material or denser material on their path from the annihilation site to the detectors are more likely to be absorbed or scattered (i.e., attenuated) than gamma rays that travel through sparser parts of the body. To this end, dual energy X-ray computed tomography (CT) can be used to generate a three-dimensional map of material components and density as a function of position. With the scattering and attenuation properties of different material components known, the reconstructed CT images can then be used to determine the gamma-ray attenuation and scattering cross-sections as a function of position (i.e., an attenuation map/image and a scatter cross-section map/image).

If images are reconstructed from sinograms without attenuation correction, then gamma rays from less dense areas (e.g., lungs) are over-represented (e.g., appear as though they are emitting more gamma rays than they actually are) and denser tissue are under-represented. In the absence of attenuation correction, the reconstructed image would be susceptible to artifacts that both impair the visual appearance of the image and also lead to inaccurate quantitation of tracer uptake.

To apply attenuation correction, an attenuation map is generated whereby one can determine the attenuation through the patient for all LORs. For example, on a stand-alone PET scanner, this can be done with a transmission scan in which an external positron source is rotated around the patient and the attenuation of the transmitted gamma rays is determined. In a combination PET/CT scanner, the acquired CT image can be used for PET attenuation correction. Further, in certain implementations, a joint-estimation method can be used to simultaneously derive both the attenuation map and the activity distribution for the PET data.

Like the attenuation map, a map of the scatter cross-section as a function of position can also be used to improve the image quality of PET images by accounting for the background signal in the PET reconstruction process. For example, the PET image can be reconstructed using a maximum-likelihood expectation maximization (ML-EM) method by iteratively updating the reconstructed image f according to the equation $$\overline{f}_j^{k+1} = \frac{\overline{f}_j^k}{\sum_i H_{ij}} \sum_i H_{ij} \frac{g_i}{\sum_{n=0}^{N-1} H_{in} \overline{f}_n^k + s_i}$$

wherein $g_i$ is the measured counts in ith LOR, H is the system matrix, $\overline{f}_j^k$ is the estimated activity in jth voxel at kth iteration, and the mean background signal is denoted by $s_i$, which includes counts due to random events and scatter events. The methods described herein provide a better (e.g., faster and/or less noisy) estimate of $s_i$ by using a radiative transfer equation (RTE).

As introduced above, scatter is a main degrading factor in PET image reconstruction. Two related methods for scatter corrections —Monte Carlo simulation and Model-based single scatter simulation (SSS)—each have their respective shortcomings. The discrete nature of Monte Carlo simulation makes it inherently noise and performing a large number of Monte Carlo simulations requires significant time and computation processing that renders it impracticable for common industrial applications. SSS is relatively fast, making it the preferred approach for commercial applications of PET scatter correction, but is inherently inaccurate because it only includes single scatter estimation, thereby ignoring higher order scatter.

The methods described herein have advantages over the Monte Carlo and SSS methods because they use an RTE approach to estimate the scatter (i.e., scatter term $s_i$). Compared with the SSS approach, the methods described herein provide more accurate scatter estimation, including both total scatters for one detector in each LOR and total scatters for both two detectors in each LOR. Compared with the MC approach, the methods described herein provide a faster scatter estimation and lower noise in the estimated scatter.

Figure 2:
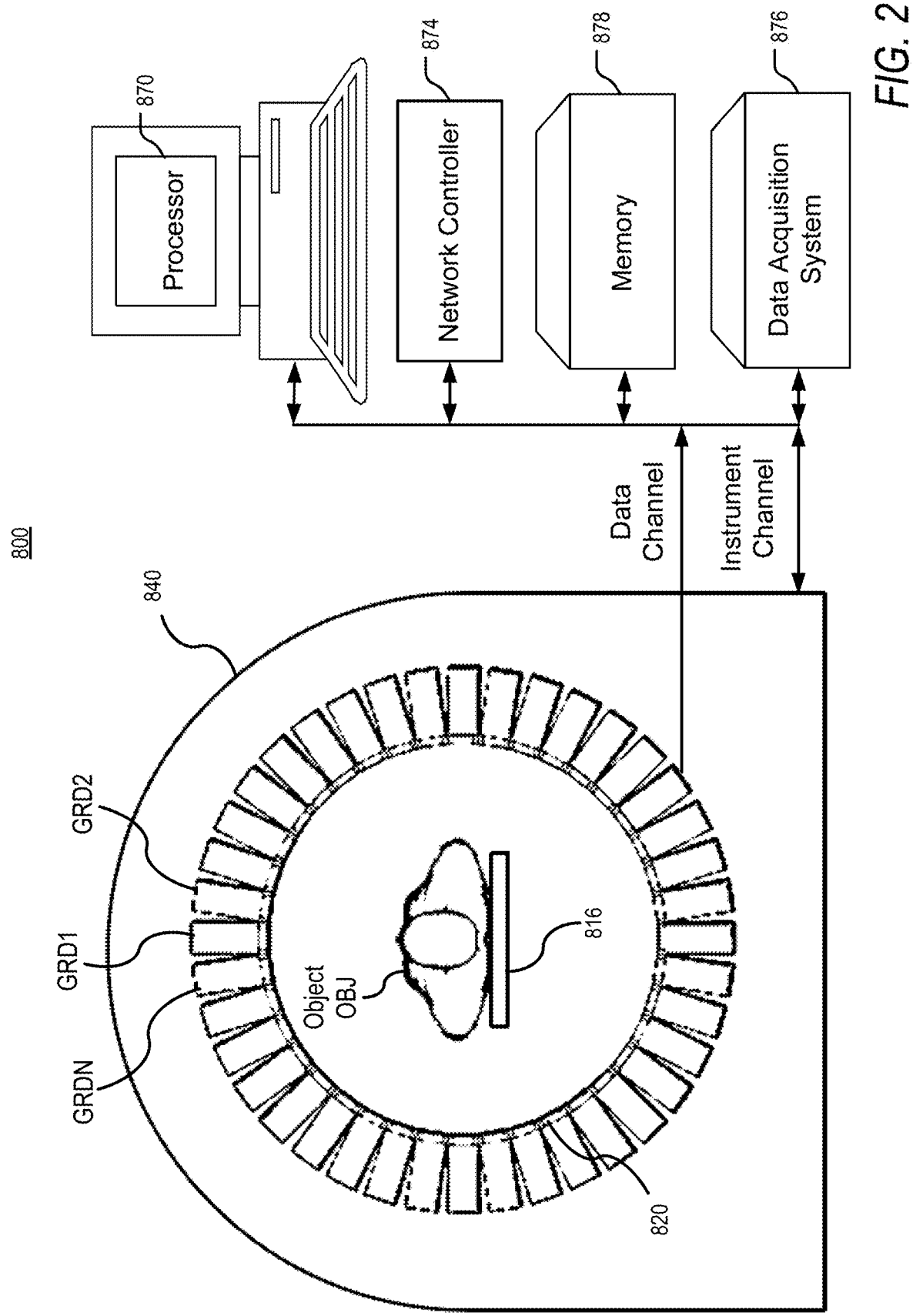
FIG. 2 is a schematic view of a PET scanner, according to an exemplary embodiment of the present disclosure.

Referring now to the Figures, wherein like reference numerals designate identical or corresponding parts throughout the several views, FIG. 1 and FIG. 2 show a PET scanner 800 including a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, the higher number of GRDs being used to create a larger bore size for the PET scanner 800. The GRDs include scintillator crystal arrays for converting the gamma rays into scintillation photons (e.g., at optical, infrared, and ultraviolet wavelengths), which are detected by photodetectors.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example. However, Anger arithmetic is not necessarily required when there is a one-to-one correspondence between the crystals and the photodetectors.

FIG. 2 shows a schematic view of a PET scanner system having GRDs arranged to detect gamma-rays emitted from an object OBJ. The GRDs can measure the timing, position, and energy corresponding to each gamma-ray detection. In one implementation, the gamma-ray detectors are arranged in a ring, as shown in FIG. 1 and FIG. 2. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 2 shows an example of the arrangement of the PET scanner 800, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to a gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

Figure 4:
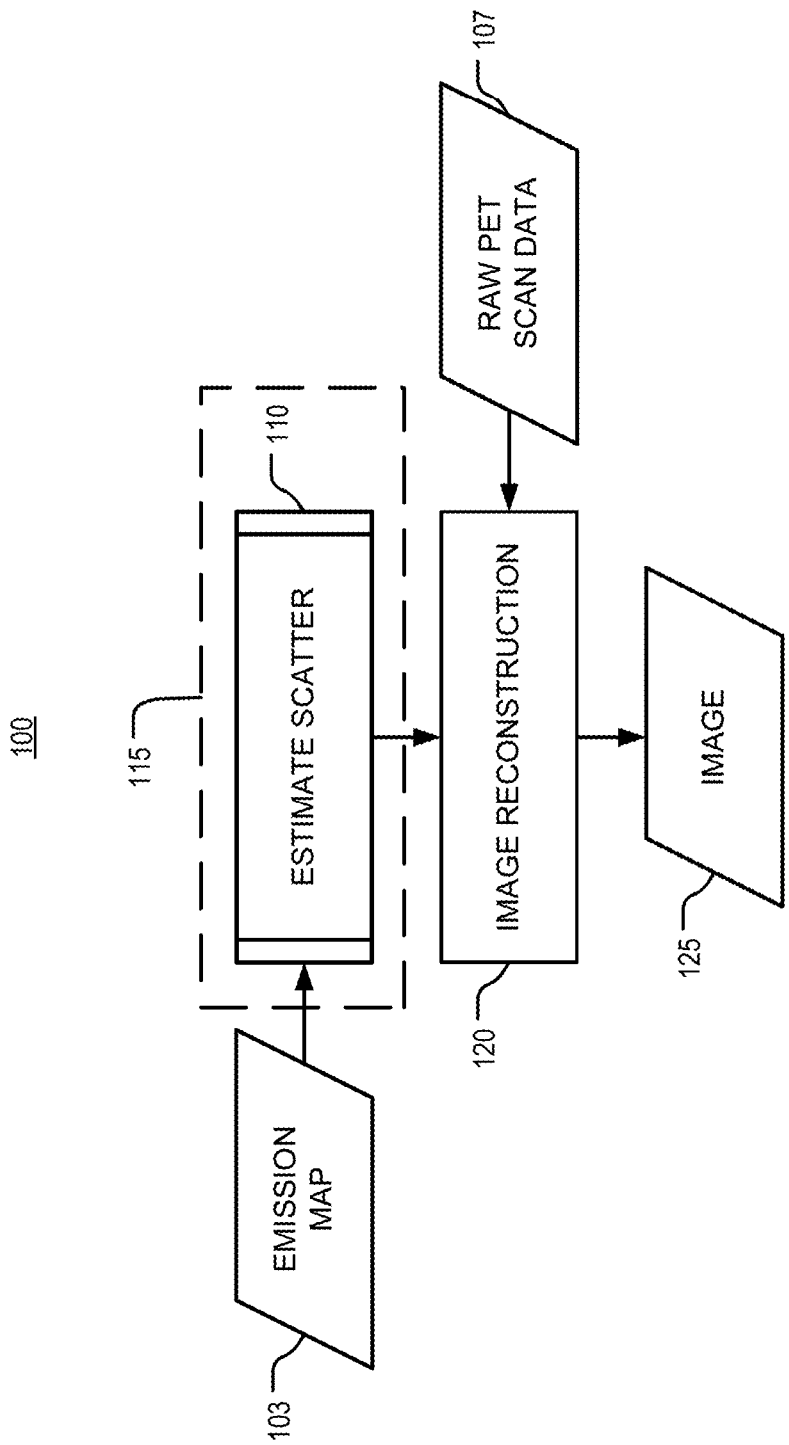
FIG. 4 is a flow diagram of a method of estimating scatter and reconstructing a PET image, according to an exemplary embodiment of the present disclosure.

In FIG. 2, circuitry and hardware is also shown for acquiring, storing, processing, and distributing gamma-ray detection data. The circuitry and hardware include a processor 870, a network controller 874, a memory 878, and a data acquisition system (DAS) 876. The PET imager also includes a data channel that routes detection measurement results from the GRDs to the DAS 876, the processor 870, the memory 878, and the network controller 874. The data acquisition system 876 can control the acquisition, digitization, and routing of the detection data from the detectors. In one implementation, the DAS 876 controls the movement of the table 816. The processor 870 performs functions including reconstructing images from the detection data in accordance with method 100 (which is illustrated in FIG. 4 and described below), pre-reconstruction processing of the detection data, and post-reconstruction processing of the image data, as discussed herein.

According to an embodiment, the processor 870 of the PET scanner 800 of FIG. 1 and FIG. 2 can be configured to perform method 100, as described herein. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 878 can be a hard disk drive, CD-ROM drive, DVD drive, FLASH drive, RAM, ROM or any other electronic storage known in the art. The memory 878 may be non-volatile, such as ROM, EPROM, EEPROM or FLASH memory. The memory 878 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform method 100 described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed image can be displayed on a display. The display can be an LCD display, CRT display, plasma display, OLED, LED or any other display known in the art.

The network controller 874, such as an Intel Ethernet PRO network interface card from Intel Corporation of America, can interface between the various parts of the PET imager. Additionally, the network controller 874 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

FIG. 3A through FIG. 3E visually represent gamma ray generation, scatter, and detection from zero-order events to higher-order events (e.g. scatter two times or more).

Figure 3A:
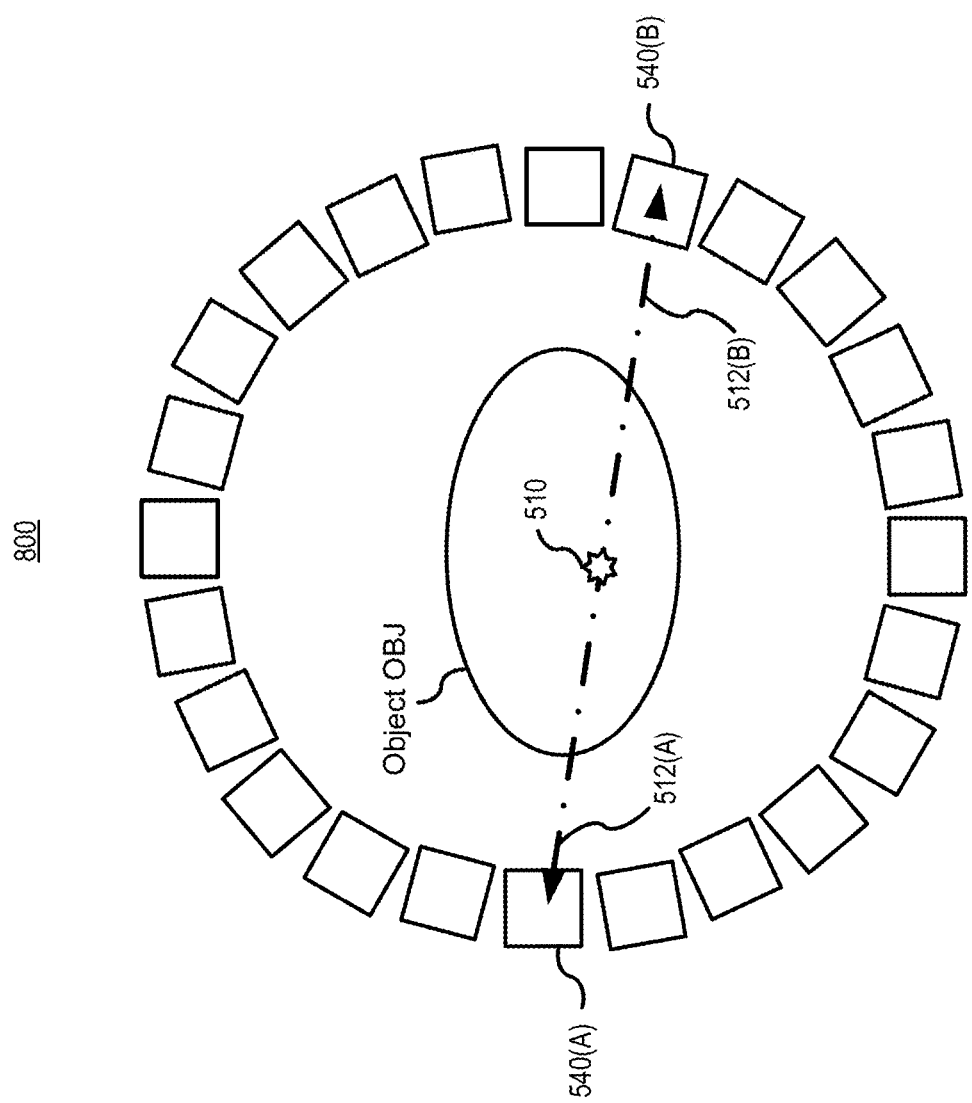
FIG. 3A is a schematic of gamma ray generation and detection in the absence of a scatter event, according to an exemplary embodiment of the present disclosure.

FIG. 3A shows a diagram of gamma ray detection in the absence of scatter. A positron annihilation 510 generates two gamma rays emitted substantially 180° apart along a first trajectory 512(A) and a second trajectory 512(B). The two gamma rays are respectively detected at a first detector 540(A) and a second detector 540(B), such that a LOR can be measured/derived between the two detectors.

Figure 3B:
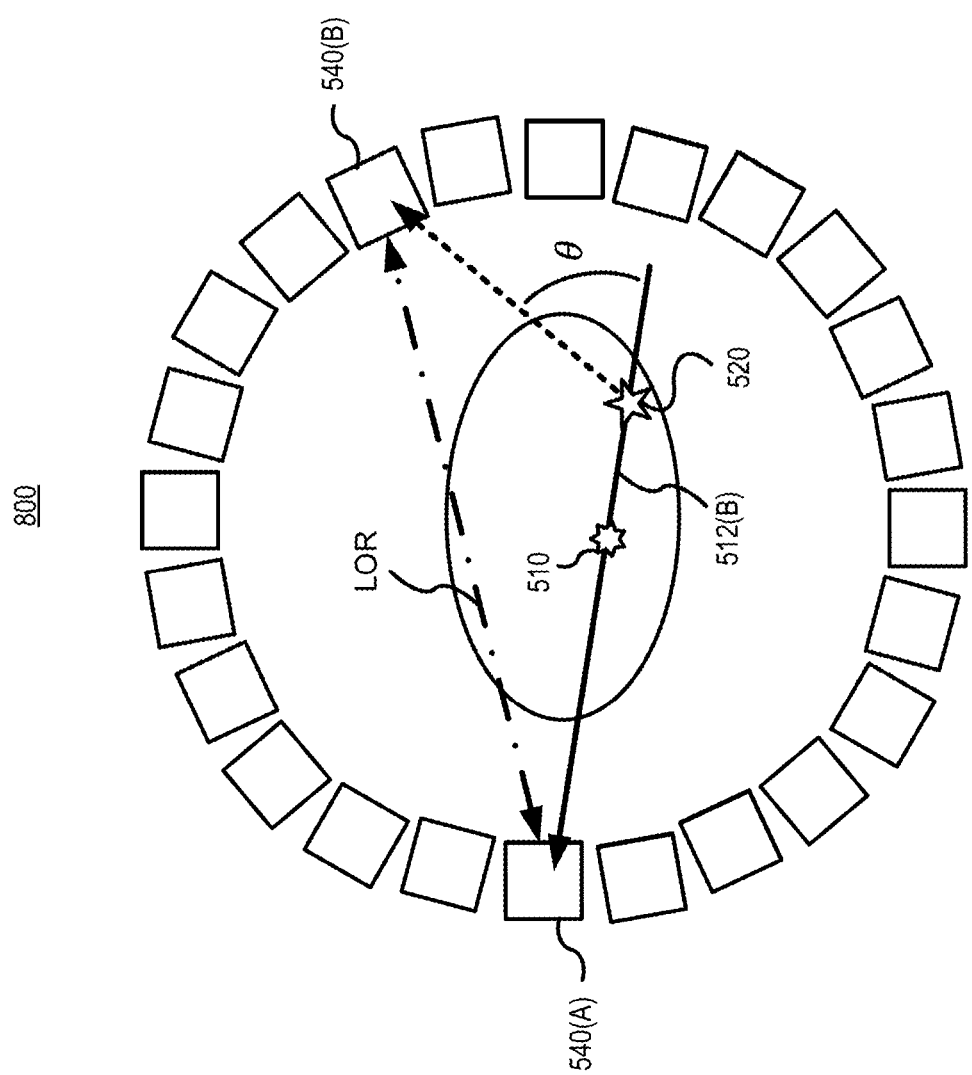
FIG. 3B is a schematic of gamma ray generation and detection of a first-order scatter event, according to an exemplary embodiment of the present disclosure.

In contrast, FIG. 3B illustrates an example when a scatter event occurs along the path of the second trajectory 512(B). Such a scatter event may be referred to herein as a variation of one-sided scatter. In this case, the gamma ray is scattered at point 520 by an angle θ, and the scattered gamma ray is detected at another second detector 540(B), such that the derived LOR does not pass through the point of the positron annihilation 510.

Figure 3C:
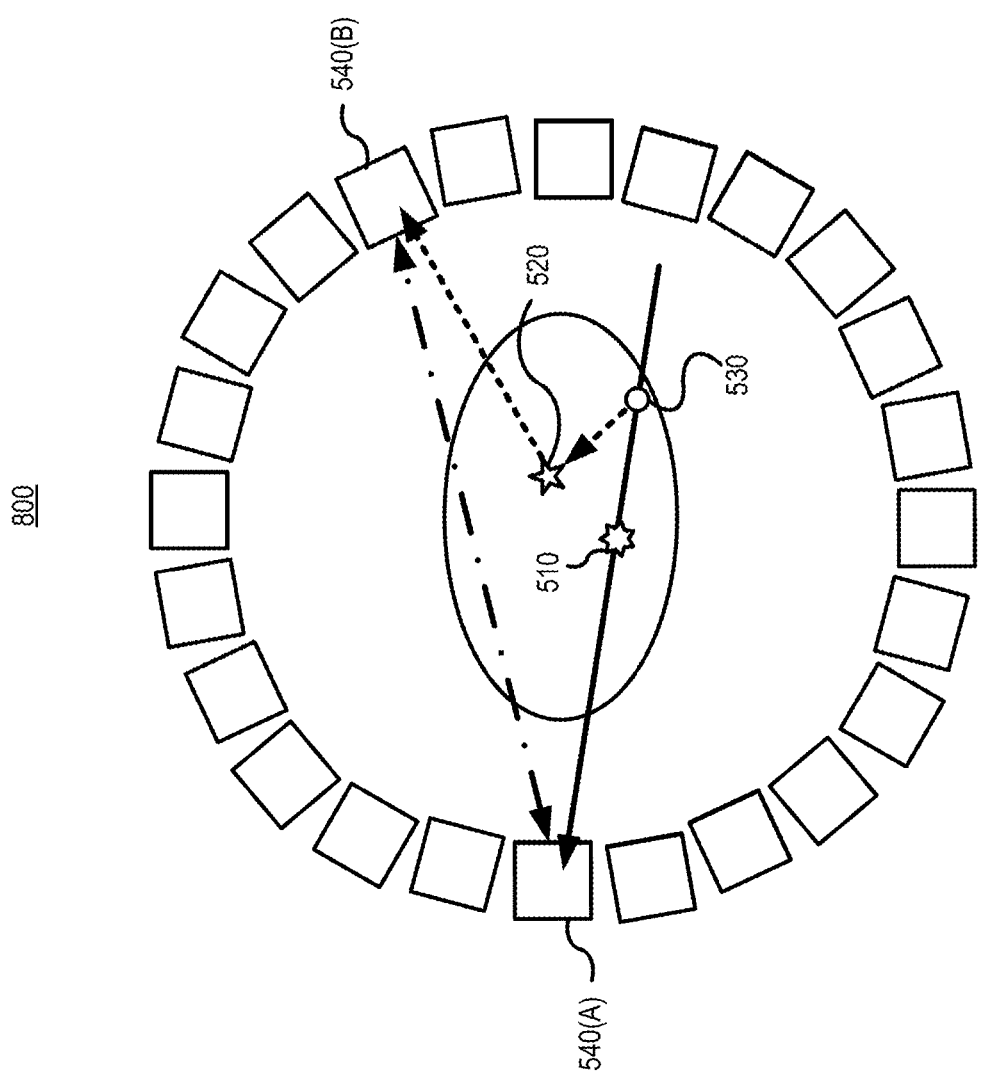
FIG. 3C is a schematic of gamma ray generation and detection of a second-order scatter event, according to an exemplary embodiment of the present disclosure.
Figure 3D:
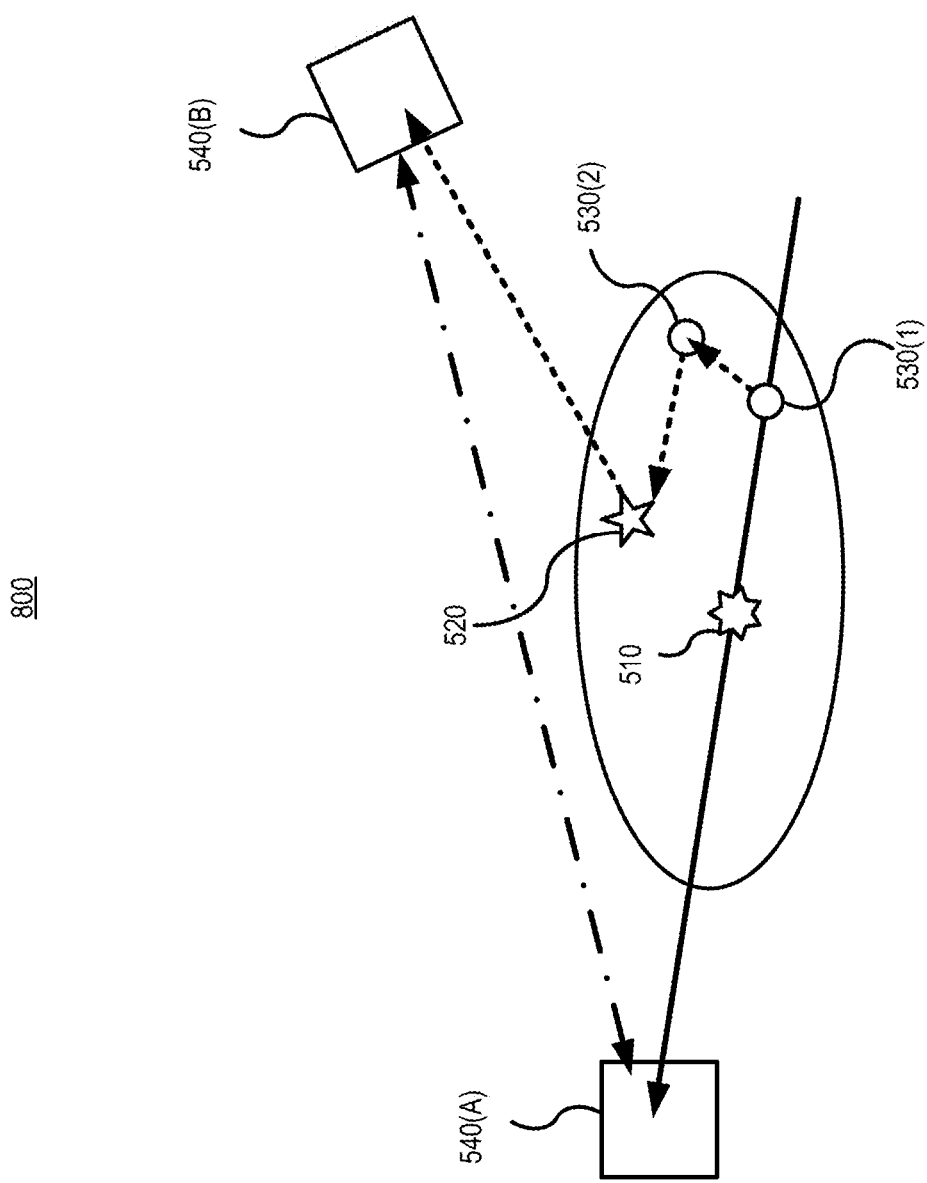
FIG. 3D is a schematic of gamma ray generation and detection of a third-order scatter event, according to an exemplary embodiment of the present disclosure.

FIG. 3C and FIG. 3D illustrate cases of higher-order scatter. FIG. 3C shows second order scatter, and FIG. 3D shows third order scatter. The scatter point 520 is the last point at which the gamma ray is scattered before being detected by the second detector 540(B). The scatter point 530 in FIG. 3C and scatter points 530(1) and 5320(2) in FIG. 3D are scatter points that occur before the final scatter point.

FIG. 3E illustrates cases of two-sided scatter wherein the gamma rays generated at positron annihilation are each scattered at least once at either point 520(A) or at point 520(B). The scattered gamma rays may then be detected at detector 540(A) and at detector 540(B) in the case of first-order scatter, wherein a LOR is formed therebetween. It can be appreciated that higher-order scatter events are possible with regard to two-sided scatter events.

The PET scanner 800 described above with respect to FIG. 1 and FIG. 2 may be configured in view of FIG. 3A through FIG. 3E to perform the methods described above and below with reference to FIG. 4, FIG. 5A, FIG. 5B, and FIG. 5C.

FIG. 4 is a flow diagram of a method 100 for estimating scatter using an RTE-based approach and reconstructing a PET image using the estimated scatter. It can be appreciated that the method 100, described with reference to FIG. 4 for a given LOR, can be applied for all LORs of a given number of detectors and a given subject volume. In this way, an iteratively reconstructed image may be generated iteratively based on scatter estimated for a single LOR of a subject volume, a predetermined region of the subject volume, or the entire volume of the subject volume.

For a given LOR (e.g., a LOR between a detector A and a detector B), the scatter can be calculated as:

$$S^{AB} = \int_{V_O} q_0 dV_O \left[ \frac{\sigma_{BO}}{4\pi R_{BO}^2} I^A + \frac{\sigma_{AO}}{4\pi R_{AO}^2} I^B + I^{AB} \right]$$

-continued where $$I^B = \varepsilon_A \left(e^{-\int_O^A \mu ds}\right)\varepsilon'_B R_B$$

reflects one-sided scatter events for detector B, and $$I^A = \varepsilon_B \left(e^{-\int_O^B \mu ds}\right)\varepsilon'_A R_A$$

reflects one-sided scatter events for detector A. For each of the above equations, and in view of FIG. 6A, A, B are detector A and detector B, respectively, O is an annihilation point, $\varepsilon_A(\varepsilon_A')$ is detector efficiency of detector A at 511 keV (i.e., scattered energy), $q_O(V_O)$ is emission density at O (i.e., emission volume), $\sigma_{AO}$ is the detector cross section normal to the photon ray between O and detector A, $R_{AO}$ is the distance from detector A to O, and $\mu$ is the linear attenuation coefficient at 511 keV. Notably, $R_A$ is the scatter flux calculated from RTE for detector A, $R_B$ is the scatter flux calculated from RTE for detector B, and $I^{AB}$ reflects two-sided scatter events for detector A and detector B from O, wherein each of two gamma rays generated at O and received at the detectors is scattered at least once.

Understanding this, and in order to determine the scatter for the given LOR between detector A and detector B, scatter flux at detectors A and B must be determined by RTE. In this way, scatter events $I^A$, $I^B$, and $I_{AB}$ may be determined.

Precise scatter solutions, including the simulation of first-order scatter and multi-order scatter flux with an accurate physical model, can be obtained using RTE as follows $$\hat{\Omega}\cdot\nabla\psi(\vec{r},E,\hat{\Omega}) + \mu(\vec{r},E)\psi(\vec{r},E,\hat{\Omega}) = \iint d\hat{\Omega}' dE' f(\vec{r},E,E',\hat{\Omega}\cdot\hat{\Omega}')\psi(\vec{r},E',\hat{\Omega}') + q(\vec{r},E,\hat{\Omega})$$

where $\psi(\vec{r}, E, \hat{\Omega})$ is the specific intensity of photon flux at point $\vec{r}$, energy E, and direction $\hat{\Omega}$, E'($\hat{\Omega}'$) and E($\hat{\Omega}$) are the incident and outgoing energy (angle) of the flux, $q(\vec{r}, E, \hat{\Omega})$ is emission map, n̂ is the normal direction of the boundary surface, $f(\vec{r}, E, E', \overline{\Omega}\cdot\overline{\Omega}')$ is the scatter cross section (for PET, only Compton scattering are considered), and $\mu(\vec{r}, E)$ is the total attenuation coefficient of different tissue from $\mu$ map. In an embodiment, the $\mu$ map may be derived from a radiographic image, such as a computed tomography image of the subject, or similar probing scan. The following emission boundary condition may be applied:

$$\psi(\vec{r}_c,E,\hat{\Omega})=0, \text{ for } \hat{n}\cdot\hat{\Omega}<0$$

In certain implementations of the RTE-based approach, the first-order scatter can be simulated as $$\psi_1(\vec{r},E,\hat{\Omega}) = \int_O^{\vec{r}} d\vec{r}' \iint d\hat{\Omega}' dE' f(\vec{r}',E,E',\hat{\Omega}\cdot\hat{\Omega}')\psi_0(\vec{r}',E',\Omega')\exp[-\int_{\vec{r}'}^{\vec{r}} d\vec{r}'' \mu(\vec{r}'',E)],$$

wherein the subscript 1 in $\psi_1(\vec{r}, E, \hat{\Omega})$ indicates the first-order scatter at point $\vec{r}$, E is an energy, and $\hat{\Omega}$ is a unit vector in the direction of propagation for the photon flux and the subscript 0 in $\psi_0(\vec{r}', E', \hat{\Omega}')$ indicates the zero-order scatter (i.e., the photon beam in the absence of scatter). Further, the annihilation point O indicates a starting point for a photon path, and $f(\vec{r}', E, E', \hat{\Omega}\cdot\hat{\Omega}')$ is the scatter cross section, which includes both Compton and Rayleigh scattering for photon PET. Finally, the variable $\mu(\vec{r}, E)$ represents the total attenuation coefficient for the photons at point $\vec{r}$ and energy E. This integral equation can be solved by discretizing the coordinates $\vec{r}$, E, $\hat{\Omega}$, $\vec{r}'$, E', $\hat{\Omega}'$, and $\vec{r}''$, and then solving numerically.

In addition to first-order scatter $\psi_1(\vec{r}, E, \hat{\Omega})$, the multiple scatter $\psi_s(\vec{r}, E, \hat{\Omega})$ can include higher-order scatter. For example, the multiple scatter can be iteratively calculated as $$\psi_s^{k+1}(\vec{r},E,\hat{\Omega}) = \psi_1(\vec{r},E,\hat{\Omega}) + \int_{\vec{r}_c}^{\vec{r}} d\vec{r}' \iint d\hat{\Omega}' dE' f(\vec{r}',E,E',\hat{\Omega}\cdot\hat{\Omega}')\psi_s^k(\vec{r}',E',\hat{\Omega}')\exp[-\int_{\vec{r}'}^{\vec{r}} d\vec{r}'' \mu(\vec{r}'',E)],$$

wherein the first term on the right-hand side is the first-order scatter and the second term on the right-hand side (i.e., the integral) represents higher-order scatter.

The scattered photon field at the detectors, located at a position $\vec{r}_D$, can then be expressed as $$\psi_s(\vec{r}_D,E,\hat{\Omega}) = \int_{\vec{r}_c}^{\vec{r}_D} d\vec{r}' \iint d\hat{\Omega}' dE' f(\vec{r}',E,E',\hat{\Omega}\cdot\hat{\Omega}')[\psi_s(\vec{r}',E',\hat{\Omega}') + \psi_0(\vec{r}',E,\hat{\Omega}')]\exp[-\int_{\vec{r}'}^{\vec{r}_D} d\vec{r}''\mu(\vec{r}'',E)].$$

In certain implementations, the scatter cross section terms $f(\vec{r}', E, E', \hat{\Omega}\cdot\hat{\Omega}')$ and the photon flux terms $\psi_s(\vec{r}', E', \hat{\Omega}')$ and $\psi_0(\vec{r}', E', \hat{\Omega}')$ in the integrand can be expanded and expressed using the lowest-order spherical harmonics terms in series expansion, simplifying the calculations. For example, the first-scatter flux can be calculated by a discretized integral formula, which is given by $$\psi_1(\vec{r}, E, l, m) = \iiint d^3\vec{r}' \exp\left[-\int_{\vec{r}'}^{\vec{r}} d\vec{r}'' \mu(\vec{r}'', E')\right] \frac{1}{|\vec{r}-\vec{r}'|^2} Y_{lm}^*(\hat{\Omega}) \times$$

$$\int dE' f(\vec{r}, E, E', \hat{\Omega}\cdot\hat{\Omega}')\psi_c\left(\vec{r}_c, E', \hat{\Omega}'\exp\left[-\int_{\vec{r}_c}^{\vec{r}'} d\vec{r}''\mu(\vec{r}'', E')\right]\right)$$

wherein $Y_{lm}^*(\hat{\Omega})$ is the complex conjugation of a spherical harmonic function of degree l and order m, and $\psi_1(\vec{r}, E, l, m)$ is the intensity of the first-scatter flux in the spherical-harmonics domain. The spherical harmonics can be given by $$Y_{lm}(\hat{\Omega}) = Y_{lm}(\theta,\phi) = N \exp(im\phi) P_l^m(\cos(\theta))$$

wherein $Y_{lm}(\hat{\Omega})$ is a spherical harmonic function of degree l and order m, $P_l^m$ is an associated Legendre polynomial, N is a normalization constant, and $\theta$ and $\phi$ represent colatitude and longitude, respectively. The number of spherical harmonics used to approximate the first-scatter flux can depend on the material component and scatter cross-section at the point $\vec{r}'$ and on the type of scattering (e.g., Compton and Raleigh scattering).

Further, the flux of multiple scatters can be calculated using a discretized integral spherical harmonics formula, which is given by $$\psi_s^{k+1}(\vec{r}, E, l, m) =$$

$$\psi_1(\vec{r}, E, l, m) + \iiint d^3 \psi_s^k \vec{r}' \exp\left[-\int_{\vec{r}'}^{\vec{r}} d\vec{r}'' \mu(\vec{r}'', E)\right] \frac{1}{|\vec{r}-\vec{r}'|^2} Y_{lm}^*(\hat{\Omega}) \times$$

-continued $$\sum_{E'}\sum_{\bar{l}} f(\vec{r}', E, E', \bar{l}) \sum_{m} Y_{\bar{l}m}(\hat{\Omega}) \psi_s^k(\vec{r}', E', \bar{l}, \bar{m})$$

wherein $\omega_s^{k+1}(\vec{r}, E, 1, m)$ and $\psi_s^k(\vec{r}', E', \vec{l}, \vec{m})$ are the intensity of the flux for multiple scatter including all scatter events up to order k+1 and order k respectively and $f(\vec{r}', E, E', \bar{l})$ is the $\bar{l}$-th coefficient when the scatter cross-section is expanded using the Legendre polynomials. By defining $$A = \int\int\int d^3\vec{r}' \exp\left[-\int_{\vec{r}'}^{\vec{r}} d\vec{r}'' \mu(\vec{r}'', E')\right]$$

$$\frac{1}{|\vec{r}-\vec{r}'|^2} Y_{\bar{l}m}^*(\hat{\Omega}) \times \sum_{E'}\sum_{\bar{l}} f(\vec{r}', E, E', \bar{l}) \sum_{m} Y_{\bar{l}m}(\hat{\Omega})$$

the above-defined iterative formula can be more simply expressed as $\psi_s^{k+1} = A\psi_s^k + \psi_1$.

Accordingly, scatter can be accurately simulated by including both the first-scatter flux and the multiple-scatter flux in order to represent an accurate physical model.

Returning now to FIG. 4, scatter, as outlined above, may be estimated at sub process 110 of method 100. In other words, for a given LOR 115, $R_A$ (i.e., the total one-sided scatter flux calculated from RTE for detector A), $R_B$ (i.e., the total one-sided scatter flux calculated from RTE for detector B), and $I^{AB}$ (i.e., the total two-sided scatter events for detector A and detector B from O), can be determined.

Accordingly, at sub process 110 of method 100, the first order scatter flux and higher order scatter flux for the given LOR 115 can be estimated by RTE. Estimation of scatter at sub process 110 of method 100 is informed by an emission map obtained at step 103 of method 100. The emission map obtained at step 103 of method 100 may be an initial reconstruction of the PET scan, or a 'coarse' reconstruction of the PET scan, thereby forming a basis from which scatter may be estimated at sub process 110 of method 100. Further, it can be appreciated that scatter estimation can be performed for each LOR of an associated detector A in order to determine, for example $R_B$. For instance, the multiple LORs may include a detector B, detector B', and detector B''. A similar process may be followed for $R_A$. Scatter estimation, as performed at sub process 110 of method 100, will be described in further detail with reference to FIG. 4.

At step 120 of method 100, the estimated scatter is utilized, in view of raw PET scan data, for iterative image reconstruction, or 'fine' image reconstruction. During 'fine' image reconstruction, raw PET scan data may be obtained at step 107 of method 100 and can be modified according to an ML-EM algorithm for PET. Fundamentally, the iterative update equation for the ML-EM algorithm for PET is $$\bar{f}_j^{k+1} = \frac{\bar{f}_j^k}{\sum_i H_{ij}} \sum_i H_{ij} \frac{g_i}{\sum_{n=0}^{N-1} H_{in}\bar{f}_n^k}$$

where $g_i$ is the measured counts in ith LOR and $\bar{f}_j^k$ is the estimated activity in jth voxel at kth iteration. Including scatter correction in the iterative reconstruction as estimated scatter $s_i$, in view of the above $S^{AB}$, or $$S^{AB} = \int_{V_O} q_0 dV_o \left[\frac{\sigma_{BO}}{4\pi R_{BO}^2} I^A + \frac{\sigma_{AO}}{4\pi R_{AO}^2} I^B + I^{AB}\right],$$

then the iterative update equation with scatter correction will be $$\bar{f}_j^{k+1} = \frac{\bar{f}_j^k}{\sum_i H_{ij}} \sum_i H_{ij} \frac{g_i}{\sum_{n=0}^{N-1} H_{in}\bar{f}_n^k + s_i}$$

wherein $g_i$ is the measured counts in ith LOR, H is the system matrix, $\bar{f}_j^k$ is the estimated activity in jth voxel at kth iteration, and the $S^{AB}$ is denoted by $s_i$, which includes counts due to random events and scatter events.

The above described calculation of the scatter estimation performed at sub process 110 of method 100 for a given LOR 115 and iterative (i.e. 'fine') image reconstruction at step 120 of method 100 can be iteratively performed for each given LOR 115 of a specified detector. With appropriate modifications, the above described method can also be iteratively performed for each LOR 115 of another detector of a plurality of detectors of a detector ring. In this way, an entire scan volume of a patient can be evaluated and an image reconstructed therefrom may be iteratively updated to provide a more accurate image absent scatter.

Having performed the above-described iterative image reconstruction of step 120 of method 100, the result may be used to iteratively generate a reconstructed image at step 125 of method 100.

As described above, scatter may be determined, for a given LOR 115, as $R_A$ (i.e., the total one-sided scatter flux calculated from RTE for detector A), $R_B$ (i.e., the total one-sided scatter flux calculated from RTE for detector B), and $I^{AB}$ (i.e., the total two-sided scatter events for detector A and detector B from O).

Figure 5A:
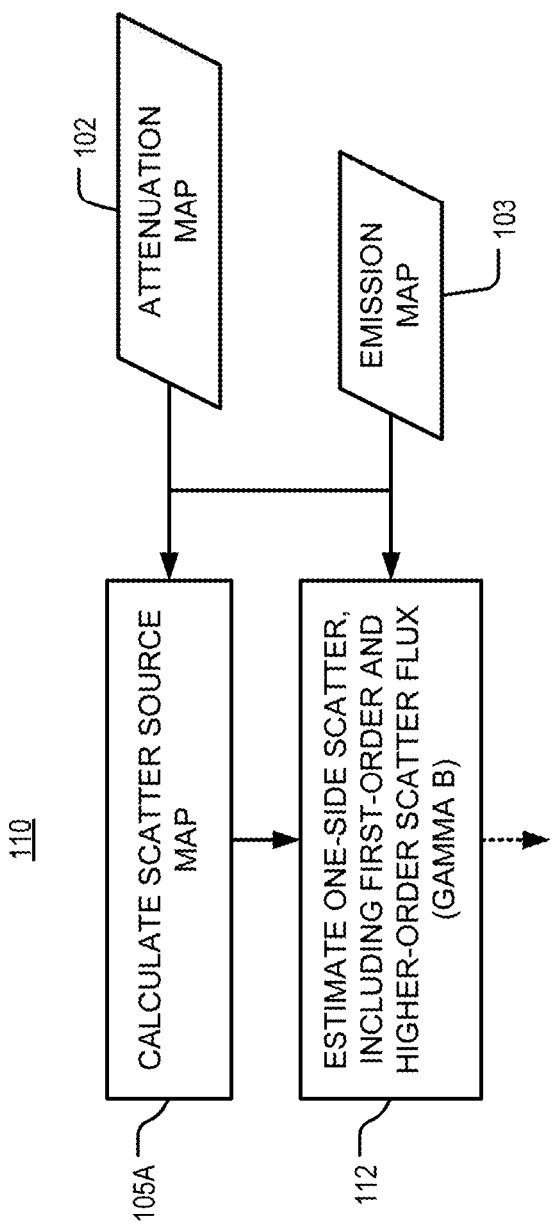
FIG. 5A is a flow diagram of a sub process of a method of reconstructing a PET image, according to an exemplary embodiment of the present disclosure.
Figure 5B:
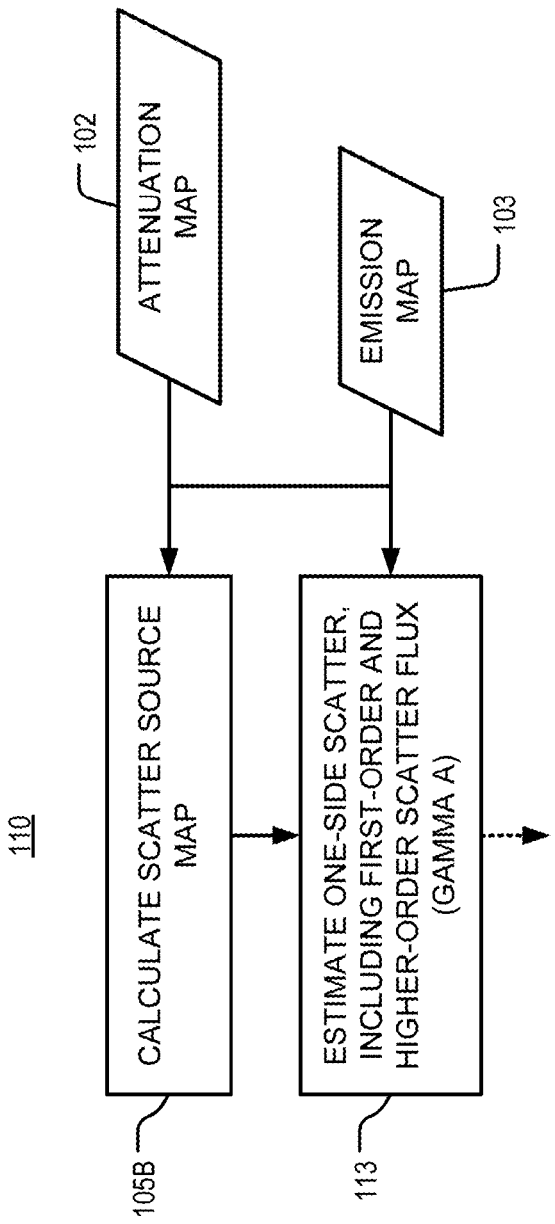
FIG. 5B is a flow diagram of a sub process of a method of reconstructing a PET image, according to an exemplary embodiment of the present disclosure.
Figure 5C:
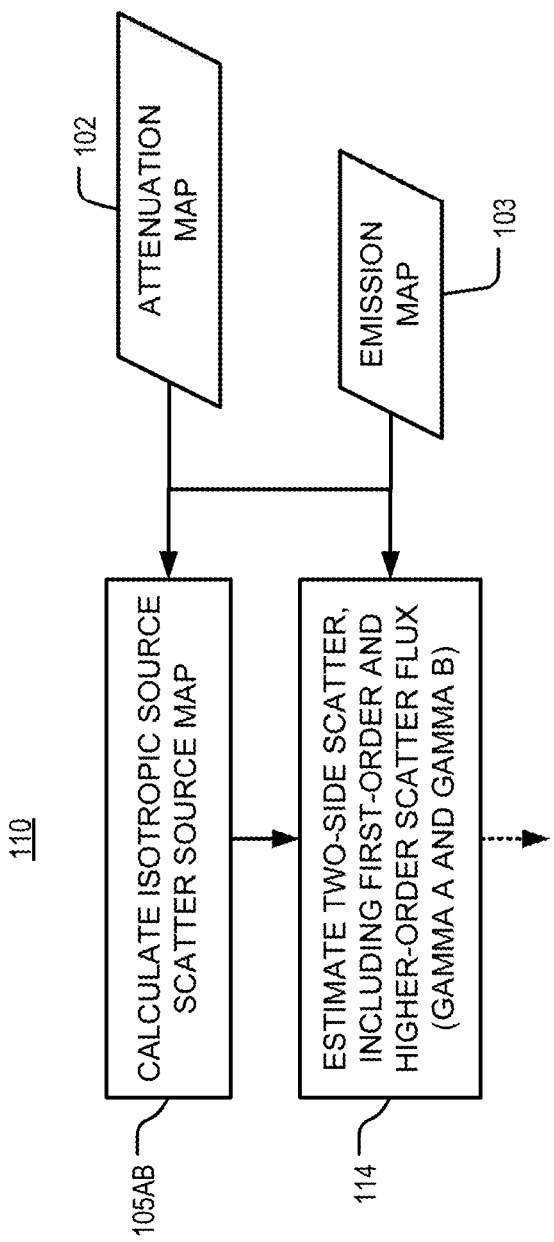
FIG. 5C is a flow diagram of a sub process of a method of reconstructing a PET image, according to an exemplary embodiment of the present disclosure.

FIG. 5A, FIG. 5B, and FIG. 5C are flow diagrams demonstrating the sub process 110 of method 100 for estimating scatter using an RTE-based approach. FIG. 5A through FIG. 5C consider a single annihilation event wherein two gamma rays, gamma A and gamma B, are generated in opposed directions.

In an embodiment, FIG. 5A estimates, with reference to a LOR between a detector A and a detector B, scatter flux detected at detector B when only gamma B is scattered. In an embodiment, FIG. 5B estimates, with reference to a LOR between a detector A and a detector B, scatter flux detected at detector A when only gamma A is scattered. In an embodiment, FIG. 5C estimates, with reference to a LOR between a detector A and a detector B, scatter flux detected at both detector A and detector B when both gamma A and gamma B are scattered. In this way, $I^A$, $I^B$, and $I^{AB}$ may be determined.

With regard to FIG. 5A, a scatter cross-section map may be calculated, using the RTE method described above, for a given LOR when only one gamma ray of an annihilation event is scattered. Described above with reference to the RTE method as a scatter cross-section map, the scatter cross-section map will be referred to below as a scatter source map, as this terminology more visually reflects that observed in the Figures. One-sided scatter, as introduced above, may be understood in view of FIG. 5A and FIG. 5B, wherein a variety of scatter sources impact a single gamma ray generated at an annihilation point. The one gamma ray of the annihilation event that is scattered may be detected at, for example, detector B. Accordingly, as described above, $R_B$ may be calculated relative to detector A by RTE.

At step 105A of sub process 110 of FIG. 5A, for instance, a scatter source map relative to detector A may be calculated using the RTE method, informed by an attenuation map obtained at step 102 of sub process 110 and an emission map obtained at step 103 of sub process 110, and implemented in the estimation of scatter detected at detector B. The scatter source map, an example of which is reflected in FIG. 6A, may be iteratively calculated on the basis of a discretization of a PET scan volume, or cross-section thereof, wherein each discretized region of the PET scan volume may be considered a scatter source. In an embodiment, the scatter source map may be determined based on, in part, a CT scan. The scatter source map (i.e. scatter cross-section map) can be calculated iteratively with $$\psi_s(\vec{r}, E, \hat{\Omega}) = \int_{\vec{r}_{q_0}}^{\vec{r}} d\vec{r}' \int \int d\hat{\Omega}' dE' f(\vec{r}', E, E', \hat{\Omega} \cdot \hat{\Omega}') [\psi_s(\vec{r}', E', \hat{\Omega}') + \psi_0(\vec{r}', E', \hat{\Omega}')] \exp\left[-\int_{\vec{r}'}^{\vec{r}} d\vec{r}'' \mu(\vec{r}'', E)\right]$$

and $$\psi_0(\vec{r}, E, \hat{\Omega}) = q_0(\vec{r}_{q_O}, E, \hat{\Omega}') \delta(\hat{\Omega}' - \hat{\Omega}) \exp\left[-\int_{\vec{r}_{q_O}}^{\vec{r}} d\vec{r}'' \mu(\vec{r}'', E)\right].$$

For a first calculation, or step, of the iterative process, $\psi_s(\vec{r}', E', \hat{\Omega}')$ defined above may be set to 0. Subsequent iterations of the calculations may then be determined according to the precision desired.

Having calculated the scatter source map relative to detector A at step 105A of sub process 110, the scatter flux measured at detector B, informed by an attenuation map obtained at step 102 of sub process 110 and an emission map obtained at step 103 of sub process 110, may be calculated at step 112 of sub process 110 by $$R_B = \int \int d\hat{\Omega} \int_{\vec{r}_{SS}}^{\vec{r}_{D_B}} d\vec{r}' \int \int d\hat{\Omega}' dE' f(\vec{r}', E, E', \hat{\Omega} \cdot \hat{\Omega}') \psi_s(\vec{r}', \hat{E}, \hat{\Omega}') \exp\left[-\int_{\vec{r}'}^{\vec{r}_D} d\vec{r}'' \mu(\vec{r}'', E)\right]$$

The scatter flux at detector B calculated above includes estimation of first-order and higher-order scatter flux, as illustrated in FIG. 6B.

Figure 7:
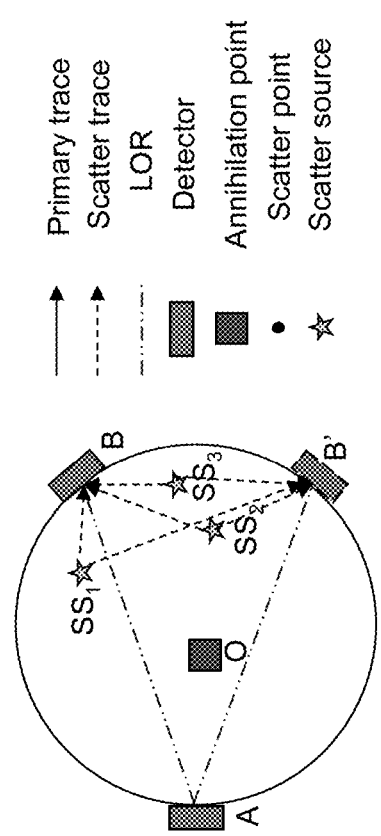
FIG. 7 is an illustration of a plurality of line-of-responses possible from a single detector A that may use an associated scatter source map, according to an exemplary embodiment of the present disclosure.

According to an embodiment, the above-described scatter source map relative to detector A may be used with a plurality of LORs originated from annihilation point O wherein detector A is included. For instance, a scatter flux estimation at detector B', detector B'', and detector B''' may be calculated according to the above-described scatter source map wherein LORs may be derived between A and B', A and B'', and A and B'''. In an example, and as shown in FIG. 7, at least two LORs may exist based on a range of detector A, the LORs including detector B and detector B'.

With regard to FIG. 5B, a scatter source map, similar to the above scatter source map of FIG. 5A, may be calculated for a given LOR when only one gamma ray of an annihilation event is scattered. Such one-sided scatter may be understood in view of FIG. 6A and FIG. 6B, wherein a variety of scatter sources impact a single gamma ray generated at an annihilation point. The one gamma ray of the annihilation event that is scattered may be detected at, for example, detector A. Accordingly, as described above, $R_A$ may be calculated relative to detector B by RTE.

At step 105B of sub process 110 of FIG. 5B, for instance, a scatter source map relative to detector B may be calculated using RTE, informed by an attenuation map obtained at step 102 of sub process 110 and an emission map obtained at step 103 of sub process 110, and implemented in the estimation of scatter detected at detector A. The scatter source map may be iteratively calculated on the basis of a discretization of a PET scan volume, or cross-section thereof, wherein each discretized region of the PET scan volume may be considered a scatter source. In an embodiment, the scatter source map may be determined based on, in part, a CT scan. The scatter source map (i.e., scatter cross section) can be calculated iteratively with $$\psi_s(\vec{r}, E, \hat{\Omega}) = \int_{\vec{r}_{q_0}}^{\vec{r}} d\vec{r}' \int \int d\hat{\Omega}' dE' f(\vec{r}', E, E', \hat{\Omega} \cdot \hat{\Omega}') [\psi_s(\vec{r}', E', \hat{\Omega}') + \psi_0(\vec{r}', E', \hat{\Omega}')] \exp\left[-\int_{\vec{r}'}^{\vec{r}} d\vec{r}'' \mu(\vec{r}'', E)\right]$$

and $$\psi_0(\vec{r}, E, \hat{\Omega}) = q_0(\vec{r}_{q_O}, E, \hat{\Omega}') \delta(\hat{\Omega}' - \hat{\Omega}) \exp\left[-\int_{\vec{r}_{q_O}}^{\vec{r}} d\vec{r}'' \mu(\vec{r}'', E)\right].$$

For a first calculation, or step, of the iterative process, $\psi_s(\vec{r}', E', \hat{\Omega}')$ defined above may be set to 0. Subsequent iterations of the calculations may then be determined according to the precision desired.

Having calculated the scatter source map relative to detector B at step 105B of sub process 110, the scatter flux measured at detector A, informed by an attenuation map obtained at step 102 of sub process 110 and an emission map obtained at step 103 of sub process 110, may be calculated at step 113 of sub process 110 by $$R_A = \int \int d\hat{\Omega} \int_{\vec{r}_{SS}}^{\vec{r}_{D_A}} d\vec{r}' \int \int d\hat{\Omega}' dE' f(\vec{r}', E, E', \hat{\Omega} \cdot \hat{\Omega}') \psi_s(\vec{r}', \hat{E}, \hat{\Omega}') \exp\left[-\int_{\vec{r}'}^{\vec{r}_D} d\vec{r}'' \mu(\vec{r}'', E)\right]$$

The scatter flux at detector A calculated above includes estimation of first-order and higher-order scatter flux.

According to an embodiment, the above-described scatter source map relative to detector B may be used with a plurality of LORs originated from annihilation point O wherein detector B is included. For instance, a scatter flux estimation at detector A', detector A'', and detector A''' may be calculated according to the above-described source map wherein LORs may be derived between B and A', B and A'', and B and A'''. In an example, at least two LORs may exist based on a range of detector B, the LORs including detector A and detector A'.

Having calculated, at FIG. 5A and FIG. 5B, each of one-sided scatter detected at detector A and detector B along the LOR, representing $I^A$ and $I^B$, a two-sided scatter event wherein both gamma A and gamma B are scattered must be accounted for. To this end, $I^{AB}$, representing scatter events at each of detector A and detector B, can be calculated. Initially, a scatter source map can be calculated at step 105AB of sub process 110, informed by an attenuation map obtained at step 102 of sub process 110 and an emission map obtained at step 103 of sub process 110. The scatter source map (i.e., scatter cross-section map) calculated at step 105AB of sub process 110 may be an isotropic source scatter cross-section map calculated using $$\psi_0(\vec{r}, E, \hat{\Omega}) = q0(\vec{r}_{q0}E, \hat{\Omega}') \exp[-\int_{\vec{r}_q}^{\vec{r}} 0^{\vec{r}} d\vec{r} \mu(\vec{r}'', E)]$$

Figures 8A, 8B:
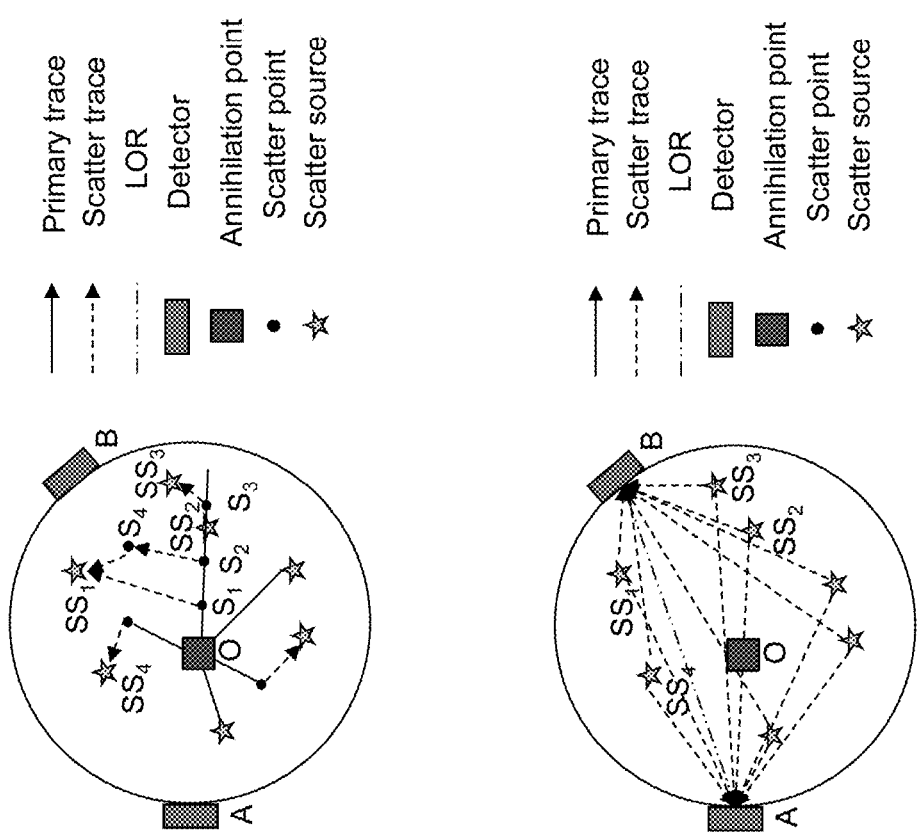
FIG. 8A is an illustration of a calculated isotropic source scatter source map, according to an exemplary embodiment of the present disclosure.
FIG. 8B is an illustration of estimated scatter flux at a detector A and a detector B, according to an exemplary embodiment of the present disclosure.

An example of an isotropic source scatter cross-section map is shown in FIG. 8A. With the isotropic source scatter cross-section map calculated at step 105AB of sub process 110, scatter flux detected at each of detector A and detector B, shown in FIG. 8B, may be estimated at step 114 of sub process 110, informed by an attenuation map obtained at step 102 of sub process 110 and an emission map obtained at step 103 of sub process 110. Scatter may be estimated by using each of $$R_A = \iint d\hat{\Omega} \int_{\vec{r}_{SS}}^{\vec{r}_{D_A}} d\vec{r}' \iint d\hat{\Omega}' dE' f(\vec{r}', E, E',$$

$$\hat{\Omega} \cdot \hat{\Omega}') \psi_s(\vec{r}', \hat{E}, \hat{\Omega}') \exp\left[-\int_{\vec{r}'}^{\vec{r}_D} d\vec{r}'' \mu(\vec{r}'', E)\right]$$

and $$R_B = \iint d\hat{\Omega} \int_{\vec{r}_{SS}}^{\vec{r}_{D_B}} d\vec{r}' \iint d\hat{\Omega}' dE' f(\vec{r}', E, E',$$

$$\hat{\Omega} \cdot \hat{\Omega}') \psi_s(\vec{r}', \hat{E}, \hat{\Omega}') \exp\left[-\int_{\vec{r}'}^{\vec{r}_D} d\vec{r}'' \mu(\vec{r}'', E)\right]$$

The scatter fluxes calculated above for each of detector A and detector B include an estimation of first-order and higher-order scatter flux.

According to an embodiment, the above-described isotropic source scatter cross-section map may be used with a plurality of LORs originated from annihilation point O.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for reconstructing an image in positron emission tomography, comprising:
   processing circuitry configured to
      acquire an emission map and an attenuation map, each representing an initial image reconstruction of a positron emission tomography scan,
      calculate, using a radiative transfer equation (RTE) method, a scatter source map of a subject of the positron emission tomography scan based on the emission map and the attenuation map,
      estimate, using the RTE method and based on the emission map, the attenuation map, and the scatter source map, scatter, and
      perform an iterative image reconstruction of the positron emission tomography scan based on the estimated scatter and raw data from the positron emission tomography scan of the subject.

2. The apparatus according to claim 1, wherein the estimated scatter includes contributions from a first-order scatter flux term and a higher-order scatter flux term.

3. The apparatus according to claim 1, wherein the attenuation map is based on a computed tomography scan of the subject.

4. The apparatus according to claim 1, wherein the estimated scatter is estimated based on annihilation events where only one of two generated gamma rays is scattered.

5. The apparatus according to claim 1, wherein the estimated scatter is estimated based on annihilation events where both generated gamma rays are scattered.

6. The apparatus according to claim 5, wherein the scatter source map of the subject of the positron emission tomography scan is an isotropic source scatter source map.

7. The apparatus according to claim 1, wherein the processing circuitry is configured to perform the iterative reconstruction of the positron emission tomography scan using a maximum-likelihood expectation maximization method.

8. A method for reconstructing an image in positron emission tomography, comprising:
   acquiring, by processing circuitry, an emission map and an attenuation map, each representing an initial image reconstruction of a positron emission tomography scan;
   calculating, by the processing circuitry using a radiative transfer equation (RTE) method, a scatter source map of a subject of the positron emission tomography scan based on the emission map and the attenuation map;
   estimating, by the processing circuitry using the RTE method and based on the emission map, the attenuation map, and the scatter source map, scatter; and
   performing, by the processing circuitry, an iterative image reconstruction of the positron emission tomography scan based on the estimated scatter and raw data from the positron emission tomography scan of the subject.

9. The method according to claim 8, wherein the estimated scatter includes contributions from a first-order scatter flux term and a higher-order scatter flux term.

10. The method according to claim 8, wherein the attenuation map is based on a computed tomography scan of the subject.

11. The method according to claim 8, wherein the estimating, by the processing circuitry, estimates the scatter based on annihilation events where only one of two generated gamma rays is scattered.

12. The method according to claim 8, wherein the estimating, by the processing circuitry, estimates the scatter based on annihilation events where both generated gamma rays are scattered.

13. The method according to claim 12, wherein the scatter source map of the subject of the positron emission tomography scan is an isotropic source scatter source map.

14. The method according to claim 8, wherein the performing, by the processing circuitry, performs the iterative reconstruction of the positron emission tomography scan using a maximum-likelihood expectation maximization method.

15. A non-transitory computer-readable storage medium storing computer-readable instructions that, when executed by a computer, cause the computer to perform a method for reconstructing an image in positron emission tomography, comprising:

acquiring an emission map and an attenuation map, each representing an initial image reconstruction of a positron emission tomography scan;

calculating, using a radiative transfer equation (RTE) method, a scatter source map of a subject of the positron emission tomography scan based on the emission map and the attenuation map;

estimating, using the RTE method and based on the emission map, the attenuation map, and the scatter source map, scatter; and performing an iterative image reconstruction of the positron emission tomography scan based on the estimated scatter and raw data from the positron emission tomography scan of the subject.

16. The non-transitory computer-readable medium according to claim 15, wherein the estimated scatter includes contributions from a first-order scatter flux term and a higher-order scatter flux term.

17. The non-transitory computer-readable medium according to claim 15, wherein the attenuation map is based on a computed tomography scan of the subject.

18. The non-transitory computer-readable medium according to claim 15, wherein the estimating estimates the scatter based on annihilation events where only one of two generated gamma rays is scattered.

19. The non-transitory computer-readable medium according to claim 15, wherein the estimating estimates the scatter based on annihilation events where both generated gamma rays are scattered.

20. The non-transitory computer-readable medium according to claim 19, wherein the scatter source map of the subject of the positron emission tomography scan is an isotropic source scatter source map.

* * * * *